(12) United States Patent
Kaup et al.

(10) Patent No.: US 8,007,501 B2
(45) Date of Patent: Aug. 30, 2011

(54) CURVED POSITIONING AND INSERTION INSTRUMENT FOR INSERTING A GUIDE WIRE INTO THE FEMUR

(75) Inventors: Thomas Kaup, Davos Platz (CH); Alberto Fernandez Dell'Oca, Montevideo (UY)

(73) Assignee: Synthes USA, LLC, West Chester, PA (US)

( * ) Notice: Subject to any disclaimer, the term of this patent is extended or adjusted under 35 U.S.C. 154(b) by 1419 days.

(21) Appl. No.: 11/351,833

(22) Filed: Feb. 10, 2006

(65) Prior Publication Data

US 2007/0012816 A1    Jan. 18, 2007

Related U.S. Application Data

(63) Continuation of application No. PCT/IB2004/000624, filed on Mar. 8, 2004.

(30) Foreign Application Priority Data

Aug. 13, 2003  (CH) ........................... 1395/03
Dec. 23, 2003  (CH) ............................. 26/04

(51) Int. Cl.
*B65H 57/00* (2006.01)
(52) U.S. Cl. .................................................. 606/96
(58) Field of Classification Search .............. 606/79, 606/80, 97, 98, 104, 108, 615, 96; 242/615–615.4
See application file for complete search history.

(56) References Cited

U.S. PATENT DOCUMENTS

| 3,439,671 | A |   | 4/1969  | Kuntscher        |        |
|-----------|---|---|---------|------------------|--------|
| 4,466,429 | A |   | 8/1984  | Loscher et al.   |        |
| 4,712,541 | A |   | 12/1987 | Harder et al.    |        |
| 5,112,336 | A |   | 5/1992  | Krevolin et al.  |        |
| 5,135,527 | A |   | 8/1992  | Ender            |        |
| 5,207,753 | A |   | 5/1993  | Badrinath        |        |
| 5,489,284 | A | * | 2/1996  | James et al. ..... | 606/62  |
| 5,573,538 | A | * | 11/1996 | Laboureau ........ | 606/96  |
| 5,624,447 | A | * | 4/1997  | Myers .............. | 606/96  |
| 5,951,561 | A | * | 9/1999  | Pepper et al. ..... | 606/80  |
| 6,074,392 | A | * | 6/2000  | Durham ............ | 606/67  |

(Continued)

FOREIGN PATENT DOCUMENTS

JP    2001245894    11/2001

OTHER PUBLICATIONS

International Search Report in PCT/IB2004/000624.

*Primary Examiner* — Thomas C Barrett
*Assistant Examiner* — Christopher Beccia
(74) *Attorney, Agent, or Firm* — Fay Kaplun & Marcin, LLP

(57) ABSTRACT

A curved positioning and insertion instrument for inserting a guide wire into the femur has a curved guide tube with a distal end to be placed on the trochanter and/or the medial muscle and a proximal end for inserting a guide wire. The instrument also has a holding arm that links the guide tube to a handle. A positioning hook fitted with at least one correction bore for receiving the guide wire or another guide wire is arranged at the distal end of the guide tube. This structure makes it possible to easily insert further or additional guide wires relative to a reference guide wire.

17 Claims, 10 Drawing Sheets

U.S. PATENT DOCUMENTS

| | | | | |
|---|---|---|---|---|
| 6,143,012 | A * | 11/2000 | Gausepohl | 606/185 |
| 6,273,892 | B1 | 8/2001 | Orbay et al. | |
| 6,309,396 | B1 * | 10/2001 | Ritland | 606/96 |
| 6,419,678 | B1 * | 7/2002 | Asfora | 606/96 |
| 7,029,476 | B2 * | 4/2006 | Hansson | 606/304 |
| 7,258,692 | B2 * | 8/2007 | Thelen et al. | 606/62 |
| 7,422,594 | B2 * | 9/2008 | Zander | 606/80 |
| 2004/0236341 | A1 * | 11/2004 | Petersen | 606/89 |
| 2005/0177159 | A1 * | 8/2005 | Guzman et al. | 606/67 |
| 2006/0015038 | A1 * | 1/2006 | Weymarn-Scharli | 600/585 |
| 2007/0203499 | A1 * | 8/2007 | Boucher et al. | 606/73 |

* cited by examiner

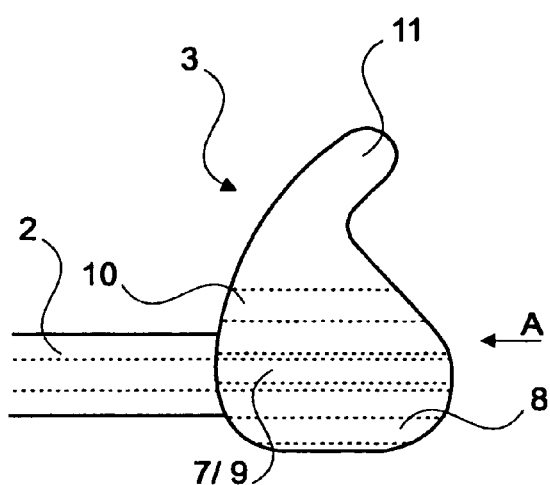
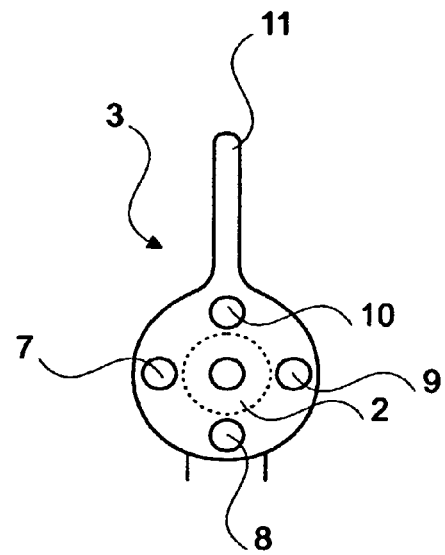
Fig.15a					Fig.15b
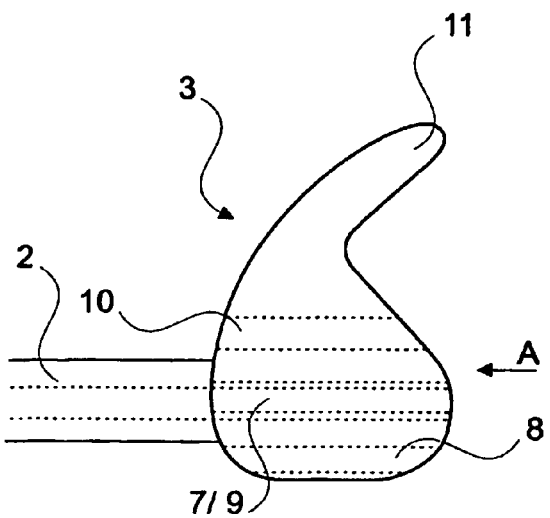
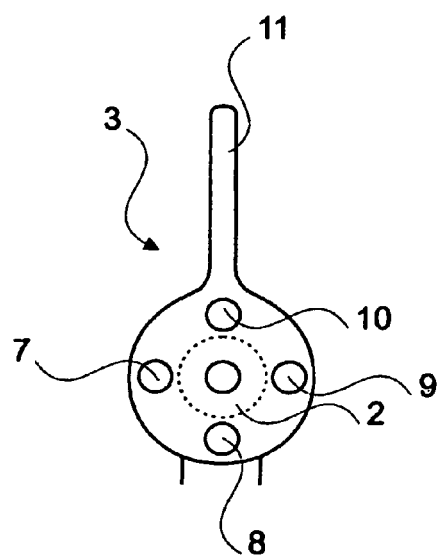
Fig.16a					Fig.16b

CURVED POSITIONING AND INSERTION INSTRUMENT FOR INSERTING A GUIDE WIRE INTO THE FEMUR

RELATED APPLICATION DATA

The present application is a continuation of the U.S. National Stage designation of co-pending International Patent Application No. PCT/IB2004/000624, filed Mar. 8, 2004, which claims priority to Swiss Patent Application Nos. 01395/03, filed Aug. 13, 2003, and 00026/04, filed Dec. 23, 2003, the entire content of which are expressly incorporated herein by reference thereto.

FIELD OF THE INVENTION

The invention relates to a curved positioning and insertion instrument for inserting a guide wire into the femur for precise bone opening.

BACKGROUND OF THE INVENTION

Precise bone opening requires a reliable reference in position and direction which a surgeon with a drill or cutter can use as a guide. It is known that guide wires which are inserted (drilled or tapped) into the femur prior to drilling in order to guide the drill safely are used for this purpose.

U.S. Pat. No. 6,074,392 describes such a curved positioning and insertion instrument for inserting a guide wire into the femur, comprising a curved guide tube having a distal end for placing on the trochanter and a proximal end for pushing in a guide wire, comprising a retaining arm for the connection between the guide tube and a handle. This design has been chosen because the insertion of a guide wire along a curve is advantageous with regard to the anatomy of the human femora, and the tissue in the affected region is therefore impaired to a lesser extent during an operation.

U.S. Pat. No. 6,074,392 therefore describes an instrument design comprising a key element which consists of a curved guide tube for a curved guide wire. This guide wire is inserted into the bone and serves as a guide path for a hollow and flexible drill. The guide wire is mounted with the aid of a positioning and insertion instrument, the curved guide tube being mounted by means of a support part on a handle which can be properly held by the surgeon. The exact positioning of the guide tube is implemented by means of X-rays or by direct inspection. After positioning, the guide wire is hammered in along the longitudinal axis of the bone or driven in in another manner. Thereafter, the insertion instrument is removed and the flexible drill or cutter is passed over the guide wire. After drilling is complete, everything is removed.

However, the weak point of this solution is that there is no particular possibility for correction if the X-ray image shows that the guide wire is not optimally positioned.

In a completely different design, for example according to U.S. Pat. No. 5,951,561, a guide instrument which has the possibility of correction of guide wires is also described. However, this design consists of a bulky sheath which receives a rotary cylindrical component comprising a plurality of discs each having a plurality of holes, which have to be oriented concentrically with one another in a complicated production process and in addition provide no possibility for tapping a guide wire along a curve into the femur. To this extent, this design offers no improvement for a design according to the generic type.

It is now the object of the invention to permit corrections by means of a simple device, the intention being to impair the tissue in the affected region as little as possible. For this reason, as already noted above, the person skilled in the art would not at all have used U.S. Pat. No. 5,951,561 as prior art for achieving the present object. It is also comprehensible that U.S. Pat. No. 6,074,392 published in 1998 is itself a further development of U.S. Pat. No. 5,624,447 published in 1997, while U.S. Pat. No. 5,951,561 was published in the same year as U.S. Pat. No. 6,074,392 and therefore followed another parallel route for setting guide wires.

Further but less relevant documents relating to the prior art are U.S. Pat. Nos. 4,466,429; 3,439,671; 5,135,527; 5,112,336; 4,712,541; and 6,273,892.

SUMMARY OF THE INVENTION

In order to achieve the object, the inventor now presents a novel positioning and insertion instrument which comprises a handle which is arranged by means of a retaining arm on a curved guide tube. At the end thereof there is a positioning hook with, if appropriate, a guide bore which is oriented at an angle of 6°-30°, preferably 7°-20°, in particular about 8°, relative to the guide tube. In addition to this bore, various correction bores are present, according to an improved further development. Furthermore, a T-handle is required when the instrument according to the invention is used. The invention thus makes it possible to insert at least one guide wire which subsequently guides an opening drill. Instead of a T-handle or a motorized drilling or tapping drive, it is also possible to provide an impact head so that the guide wire can be hammered in.

According to the invention, during use in practice, the guide tube is, if appropriate, first loaded with a reference guide wire. The handle of the positioning and insertion instrument is then aligned by visual inspection approximately parallel to the longitudinal axis of the femur and with the extension of the intramedullary canal thereof. The positioning hook is placed on the trochanter and the nose of the hook is forced by pressure in the medial direction into the muscle (gluteus medius), the reference guide wire being inserted parallel to the longitudinal axis of the femur. The instrument is removed. Thereafter, the guide tube of the positioning and insertion instrument is loaded with an opening guide wire and, according to this method of use, the guide bore in the positioning hook is pushed over the reference guide wire and thus once again placed on the trochanter. Because the guide bore in the positioning hook is set at about 8°, the positioning and insertion instrument becomes aligned accordingly in order to give the opening guide wire the correct angle. This procedure is carried out because it is more difficult to estimate a certain angle visually than a parallelism. If, however, the reference guide wire were to happen to fit the first time, it would also be possible to use it as an opening guide wire. As a rule, however, it is expected that a second guide wire has to be set as the opening guide wire.

A number of embodiments without a guide bore dispenses with the insertion of the reference guide wire and ensures the placing of the positioning and insertion instrument at the correct site and angle by the particular characteristics of its positioning hook which are adapted to the anatomical conditions. The design of these hooks is therefore chosen so that, when gently pressed into the medial muscle and when placed on the trochanter, the hook comes to rest in the optimum position for insertion of the opening guide wire in the majority of applications. The nose is designed so that it can be pressed into the medial muscle while protecting soft tissue. Its thickness is about 0.5-10 mm, preferably about 1-5 mm and in particular about 2.5 mm. The length between the centre of the guide tube and the tip of the nose of the positioning hook may vary, depending on the soft tissue situation, between about 10-30 mm, preferably about 15-25 mm, and is in particular about 20 mm. The correction bores have a diameter of about 1-5 mm, preferably about 1.8-3.6 and in particular about 3.3 mm. The receptacle for the guide tube is about 3-20 mm, preferably about 6-10 mm and in particular about 8 mm.

If the opening guide wire is also inserted into the trochanter, it is approximately at an optimum angle of about 8° relative to the reference guide wire in the frontal plane at its insertion point. X-ray images can now confirm whether the opening guide wire is in the correct position for implementing the opening. However, if it is, for example, too close to the lateral cortex there is according to the invention the possibility of a correction with the aid of the positioning and insertion instrument. This is then pushed with one of its correction bores over the reference or opening guide wire and a further, previously loaded, opening guide wire is inserted in a new position into the trochanter. The old opening guide wire which was not correctly positioned can then be removed. If required, such a correction measure can be made on the basis of the only set reference guide wire by directly pushing a correction bore, instead of the guide bore, onto the reference guide wire.

BRIEF DESCRIPTION OF THE DRAWINGS

Further developments of the invention are indicated in the figures and in the dependent patent claims. The list of reference numerals following the detailed description is part of the disclosure. The invention is explained in more detail schematically and by way of example on the basis of the figures.

The figures are described in relation to one another and as a whole. Identical reference numerals denote identical components, and reference numerals with different indices indicate functionally identical or similar components.

FIG. 15*a* schematically shows the positioning hook of the positioning and insertion instrument without guide bore and with its correction bores and the nose for retention in the medial muscle in frontal view or anterior/posterior view;

FIG. 15*b* schematically shows the positioning hook of the positioning and insertion instrument without guide bore and with its correction bores and the nose for retention in the medial muscle in view A according to FIG. 15*a*;

FIG. 16*a* schematically shows the positioning hook of the positioning and insertion instrument without guide bore and with its correction bores and the nose for retention in the medial muscle in frontal view or anterior/posterior view;

FIG. 16*b* schematically shows the positioning hook of the positioning and insertion instrument without guide bore and with its correction bores and the nose for retention in the medial muscle in view A according to FIG. 16*a*;

DETAILED DESCRIPTION OF THE PREFERRED EMBODIMENTS

Figure 1:
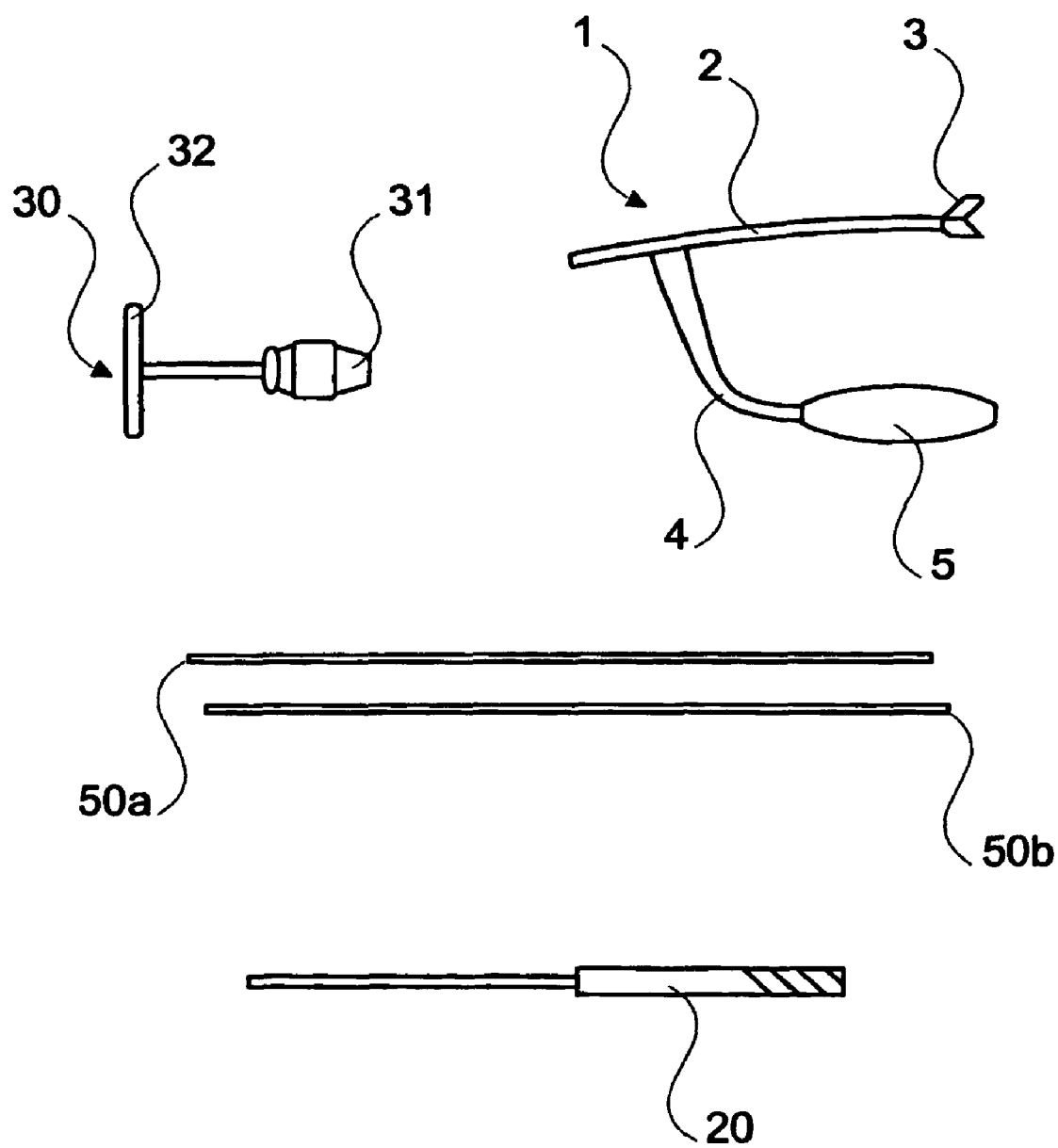
FIG. 1 schematically shows the positioning and insertion instrument having a T-handle, guide wires and an opening drill.

FIG. 1 shows the individual components which as a rule are required in using the instrument according to the invention. The positioning and insertion instrument 1 consists of a curved guide tube 2, at the distal end of which a positioning hook 3 is arranged. The curvature of the guide tube 2 describes a radius of about 300 to 800 mm, preferably 500 to 700 mm, in particular about 600 mm. The positioning hook 3 is formed in such a way that it is retained on the tip of the greater trochanter and the medial muscle. In the region of the proximal end of the guide tube 2, mounted approximately perpendicularly thereto, is a retaining arm 4 which then curves in order to run approximately parallel to the guide tube 2. A handle 5, the longitudinal axis of which is approximately parallel to a tangent to the guide tube 2 in the region of the positioning hook 3, is present at the end of the retaining arm 4. Furthermore, FIG. 1 shows two guide wires 50 which are such that they can be inserted into the guide tube 2 and can be used either as reference guide wire 50a or as opening guide wire 50b. In addition a hollow opening drill 20 is shown, which is formed in such a way that it can be passed over a guide wire 50 and can be operated by a T-handle 30. Finally, FIG. 1 shows the above mentioned T-handle 30 with a lever 32 and a drill chuck, which fits both onto the guide wires 50 and on to the opening drill 20. Of course, motor-driven drilling and tapping drives are of course also possible as an alternative to the T-handle.

Figure 2:
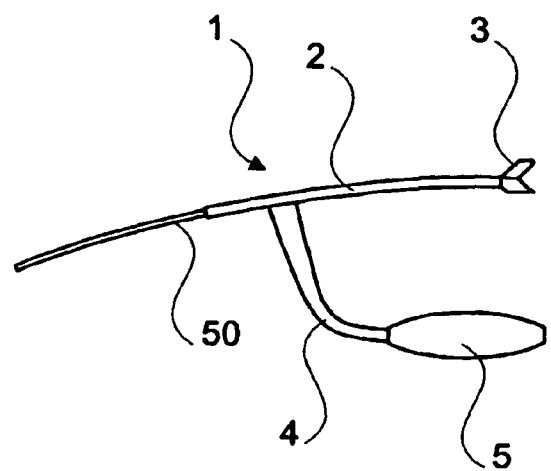
FIG. 2 schematically shows the positioning and insertion instrument with loaded guide wire.

FIG. 2 shows the positioning and insertion instrument 1 with a guide wire 50 loaded into the guide tube 2. The guide wire 50 can be inserted at the proximal or distal end of the positioning and insertion instrument 1, which leads to at least temporary curvature of the guide wire 50.

Figure 3A:
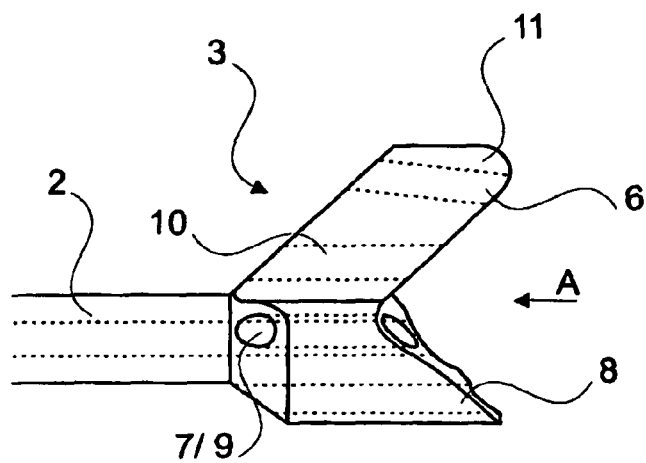
FIG. 3*a* schematically shows the positioning hook of the positioning and insertion instrument with its guide and correction bores and the nose for retention in the medial muscle in frontal view or anterior/posterior view.
Figure 3B:
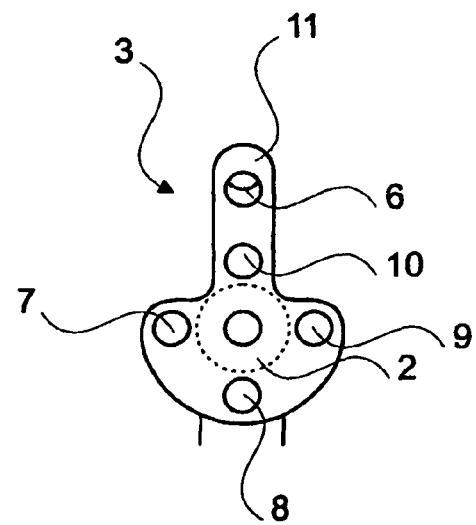
FIG. 3*b* schematically shows the positioning hook of the positioning and insertion instrument with its guide and correction bores and the nose for retention in the medial muscle in view A according to FIG. 3*a*.

FIG. 3a and FIG. 3b show the positioning hook 3 of the positioning and insertion instrument 1, comprising a guide bore 6, which is set at an angle of about 8° in the nose 11 relative to the guide tube 2 and the central bore thereof. In addition to this bore, various correction bores are present, in particular an anterior/posterior correction bore 7, a medial correction bore 8, a posterior/anterior correction bore 9 and a lateral correction bore 10.

Figure 4:
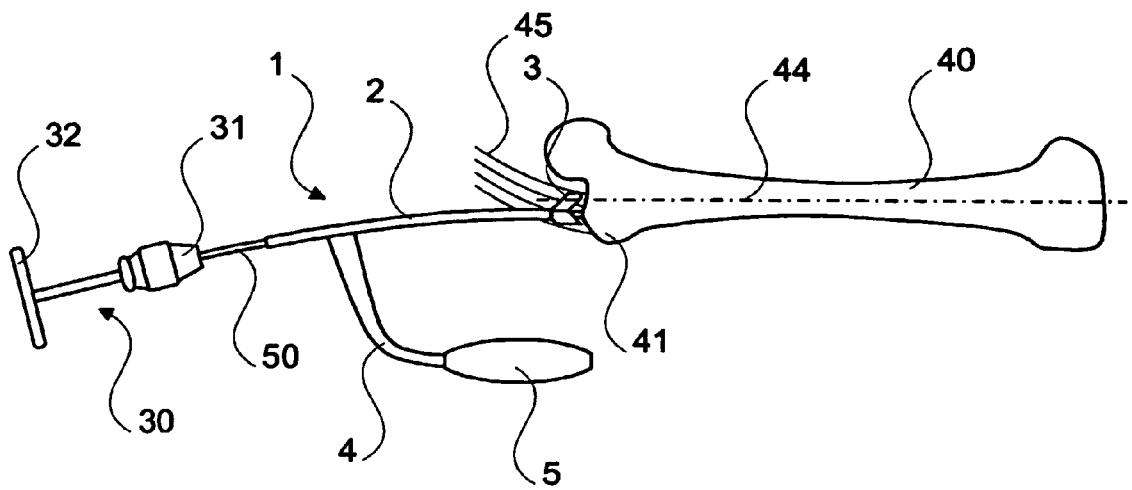
FIG. 4 schematically shows the positioning and insertion instrument with guide wire and T-handle, placed on the trochanter and ready for drilling, in frontal view or anterior/posterior view.

FIG. 4 shows the positioning and insertion instrument 1 with a guide wire 50 lowered into the guide tube 2, which instrument is placed on the greater trochanter 41 of a femur 40. The characteristics of the positioning hook 3 ensure proper non slip positioning on the surface of the trochanter 41 and in the medial muscle 45. The handle 5 of the positioning and insertion instrument 1 is aligned parallel to the longitudinal axis of the femur 40 and parallel to the extension of the intramedullary canal thereof. The T-handle 30 is shown in the position in which it is capable of inserting the guide wire 50.

Figure 5:
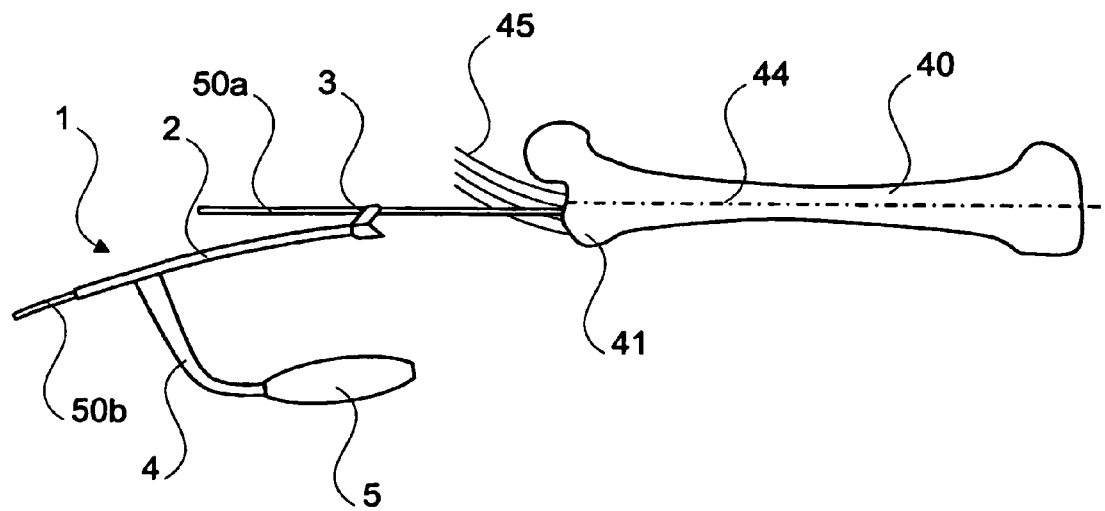
FIG. 5 schematically shows the positioning and insertion instrument loaded with the opening guide wire and pushed over the reference guide wire.

FIG. 5 shows the positioning and insertion instrument 1 which is just being pushed along its guide bore 6 on the reference guide wire 50a already inserted into the trochanter 41 of the femur 40. The positioning and insertion instrument 1 or its guide tube 2 is loaded with an opening guide wire 50b.

Figure 6:
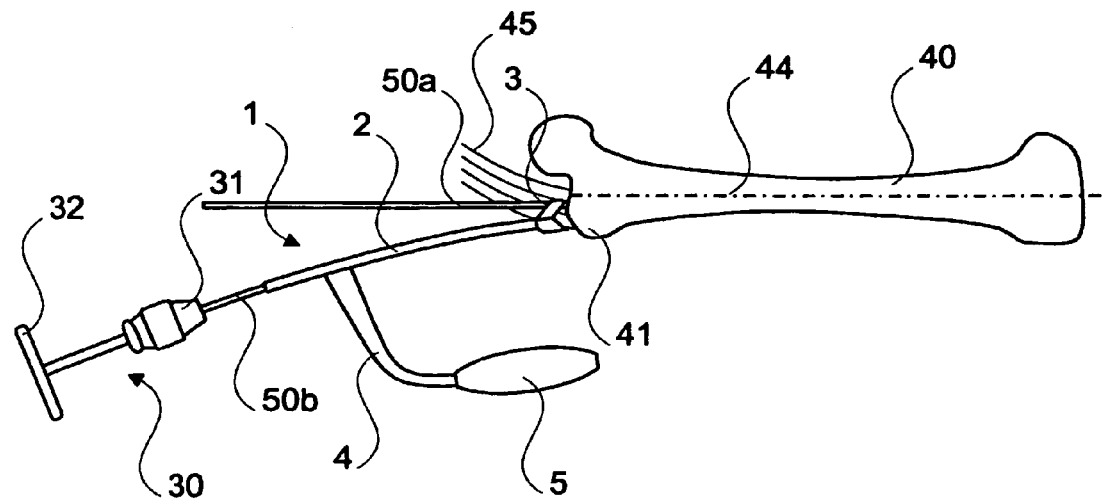
FIG. 6 schematically shows the positioning and insertion instrument with T-handle, loaded with the opening guide wire, moved over the reference guide wire and placed again on the trochanter and ready for drilling.

FIG. 6 shows the positioning and insertion instrument 1 which has been pushed through the guide bore 6 over the reference guide wire 50a already inserted into the trochanter 41 of the femur 40. The positioning and insertion instrument 1 is correctly positioned corresponding to the angle of about 8° in the frontal plane of the guide bore 6, in order to insert the already loaded opening guide wire 50b. The T-handle 30 is shown in the position in which it is capable of inserting the opening guide wire 50b.

Figure 7:
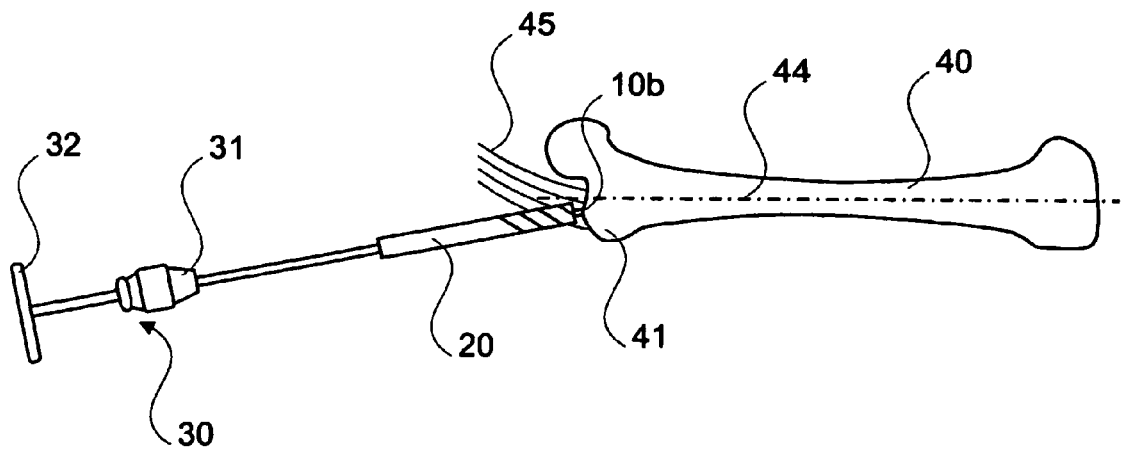
FIG. 7 schematically shows the opening drill pushed over the opening guide wire and with T-handle ready for drilling.

FIG. 7 shows the opening drill 20 when it has been pushed over the inserted opening guide wire 50b. The T-handle 30 is shown in the position in which it is capable of inserting the opening drill 20 into the trochanter 41 of the femur 40.

Figure 8:
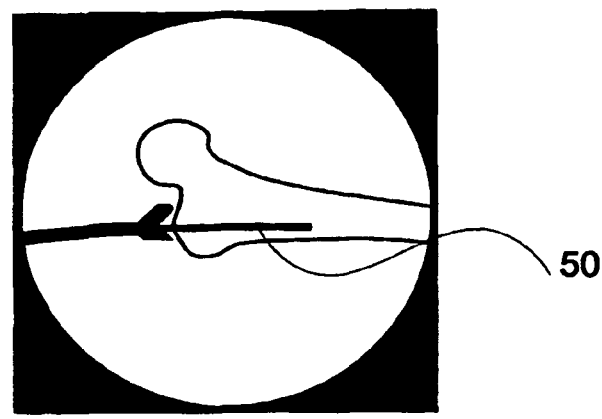
FIG. 8 schematically shows an X-ray image of the femur with inserted guide wire.

FIG. 8 shows an X-ray image which shows the positioning hook 3 of the positioning and insertion instrument 1 and a guide wire 50 loaded in the guide tube 2 and inserted into the trochanter 41 of the femur 40. Proper positioning by means of the characteristics of the positioning hook 3 on the surface of the trochanter 41 is evident. The guide wire 50 has been inserted parallel to the longitudinal axis of the femur 40 and in the intramedullary canal thereof.

Figure 9:
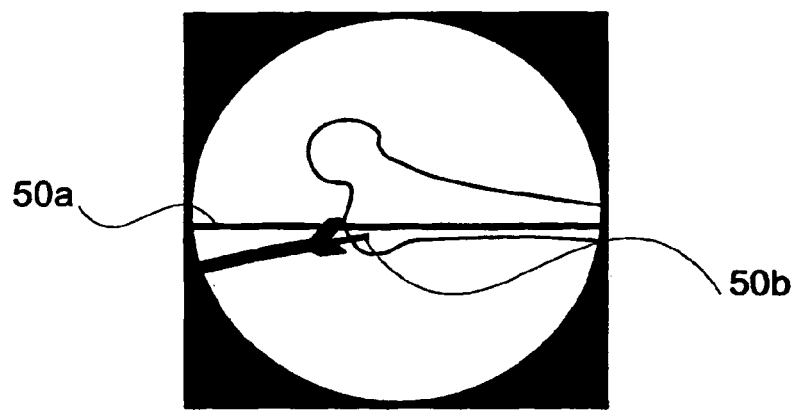
FIG. 9 schematically shows an X-ray image of the femur with inserted reference guide wire and opening guide wire to be inserted.

FIG. 9 shows an X-ray image which shows the positioning hook 3 of the positioning and insertion instrument 1, which has been pushed via its guide bore 6 over the reference guide wire 50a already inserted into the trochanter 41 of the femur 40. The positioning and insertion instrument 1, is optimally correctly positioned, corresponding to the angle of about 8°, in the frontal plane of the guide bore 6, in order to insert the already loaded opening guide wire 50b.

Figure 10:
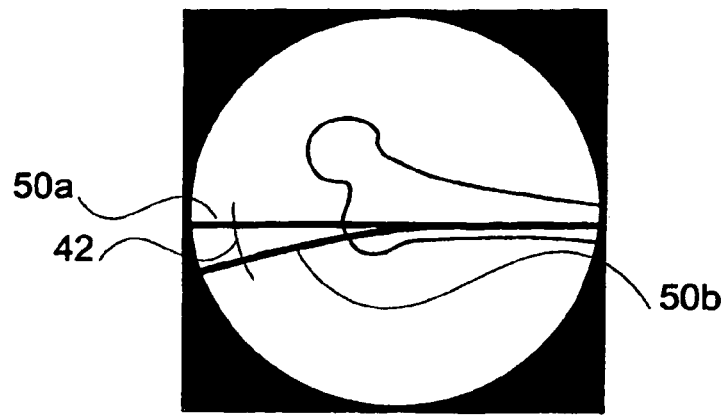
FIG. 10 schematically shows an X-ray image of the femur with inserted reference guide wire and inserted opening guide wire.

FIG. 10 shows an X-ray image which shows the reference guide wire 50a and opening guide wire 50b inserted into the trochanter 41 of the femur 40. The desired insertion angle 42 of about 8° between reference guide wire 50a and opening guide wire 50b is clearly recognisable.

Figure 11:
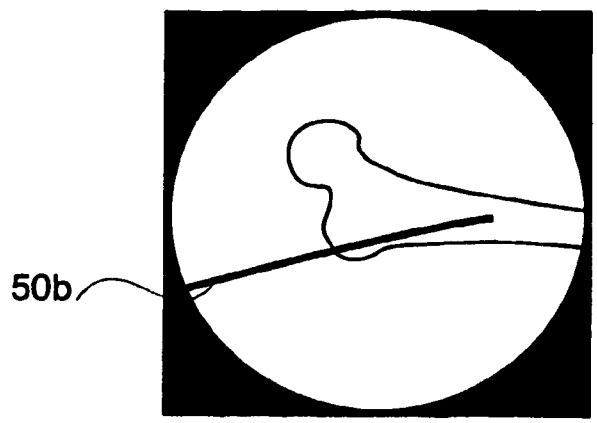
FIG. 11 schematically shows an X-ray image of the femur with inserted opening guide wire and without or optionally with removed reference guide wire.

FIG. 11 shows an X-ray image which shows the remaining opening guide wire 50b optionally after removal of the reference guide wire 50a. In this example, the opening guide wire 50b is located too close to the lateral cortex to implement the opening and has to be corrected.

Figure 12:
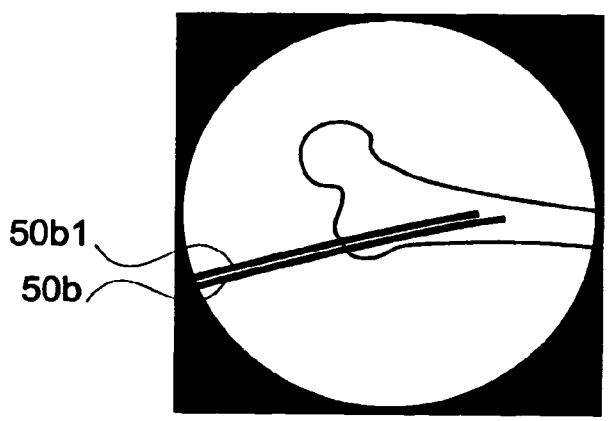
FIG. 12 schematically shows an X-ray image of the femur with non-optimally positioned first opening guide wire and second opening guide wire for correction.

FIG. 12 shows an X-ray image which shows the correction of the opening guide wire 50b. A second opening guide wire 50b is inserted into the trochanter 41 parallel to the guide wire 50b.

Figure 13:
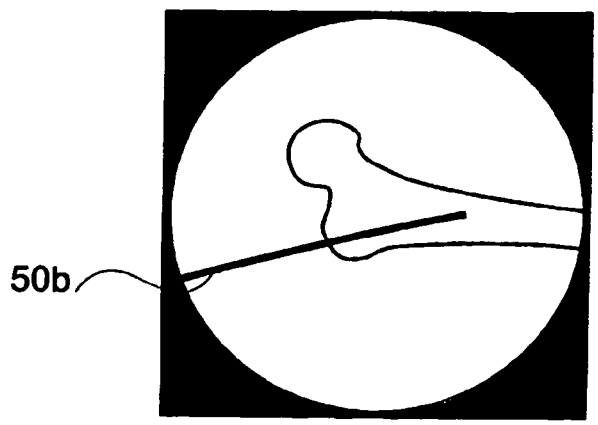
FIG. 13 schematically shows an X-ray image of the femur with correctly set opening guide wire.

FIG. 13 shows an X-ray image which shows the corrected opening guide wire 50b after removal of the first opening guide wire 50b. It is now located optimally for implementing the opening by means of opening drill 20.

Figure 14:
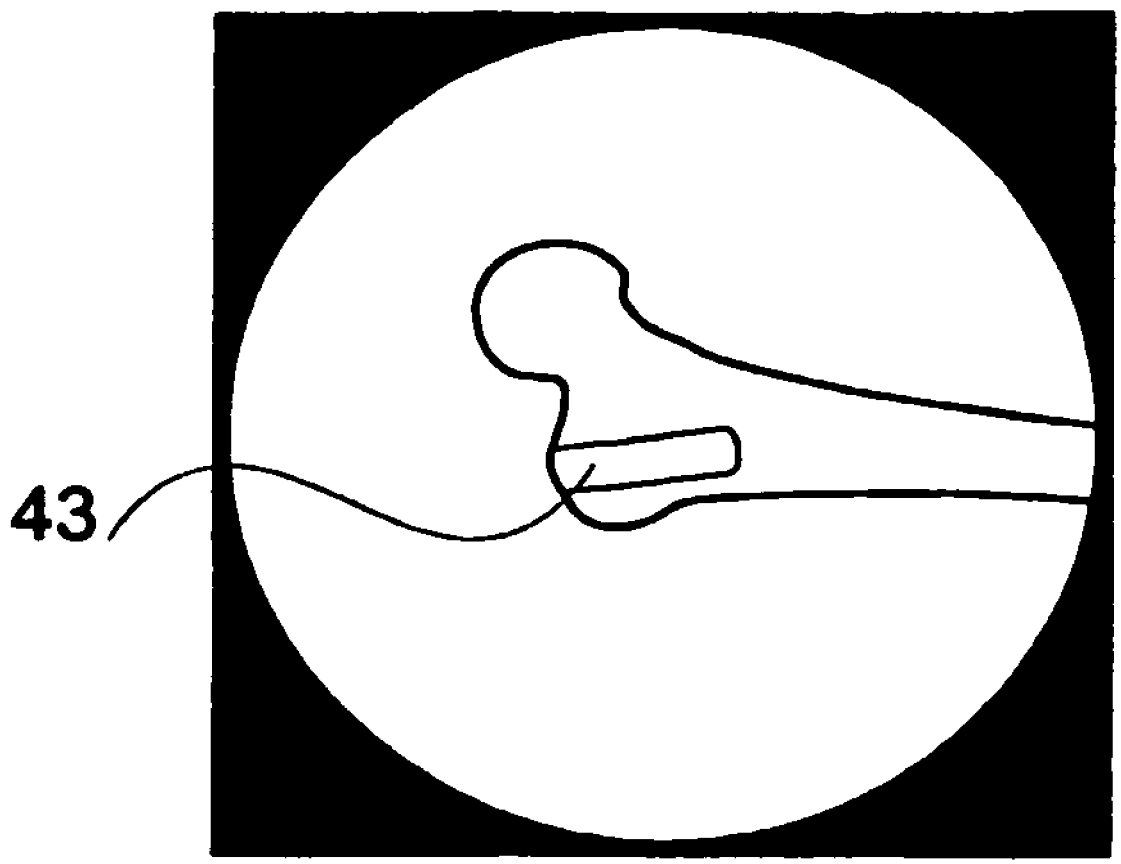
FIG. 14 schematically shows an X-ray image of the femur with opening bore.

FIG. 14 shows an X-ray image which shows the implemented opening 43 of the trochanter 41 of the femur 40.

FIG. 15a and FIG. 15b show the positioning hook 3 of the positioning and insertion instrument 1, which positioning hook has no guide bore, comprising various correction bores, in particular an anterior/posterior correction bore 7, a medial correction bore 8, a posterior/anterior correction bore 9 and a lateral correction bore 10. In comparison with the variant shown in FIG. 3a and FIG. 3b, the nose 11 is also markedly thinner.

FIG. 16a and FIG. 16b show the positioning hook 3 of the positioning and insertion instrument 1, which positioning hook has no guide bore, comprising various correction bores, in particular an anterior/posterior correction bore 7, a medial correction bore 8, a posterior/anterior correction bore 9 and a lateral correction bore 10. In comparison with the variant shown in FIG. 15a and FIG. 15b, the nose 11 tapers somewhat more sharply and is longer.

Figure 17A:
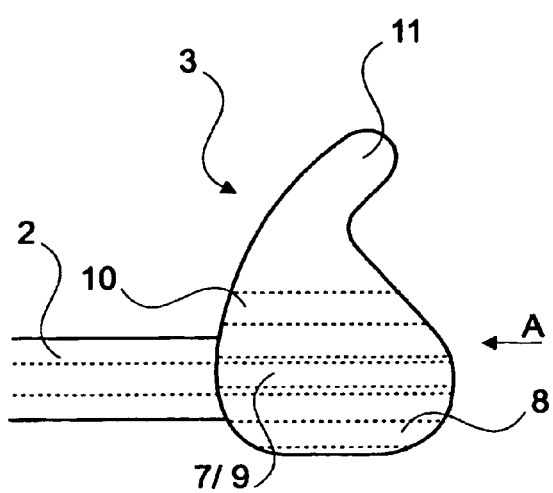
FIG. 17*a* schematically shows the positioning hook of the positioning and insertion instrument without guide bore and with its correction bores and the nose for retention in the medial muscle in frontal view or anterior/posterior view.
Figure 17B:
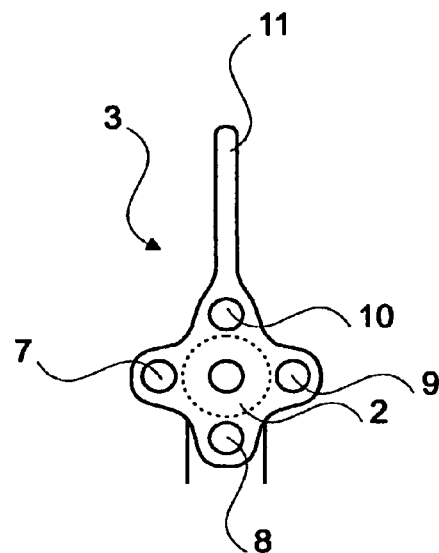
FIG. 17*b* schematically shows the positioning hook of the positioning and insertion instrument without guide bore and with its correction bores and the nose for retention in the medial muscle in view A according to FIG. 17*a*.

FIG. 17a and FIG. 17b show the positioning hook 3 of the positioning and insertion instrument 1, which positioning hook has no guide bore, comprising various correction bores, in particular an anterior/posterior correction bore 7, a medial correction bore 8, a posterior/anterior correction bore 9 and a lateral correction bore 10. This variant differs in comparison with the variants shown in FIG. 15a and FIG. 15b, FIG. 16a and FIG. 16b, substantially through a smaller cross-sectional area. The correction bores are enclosed by the outer contour.

Figure 18A:
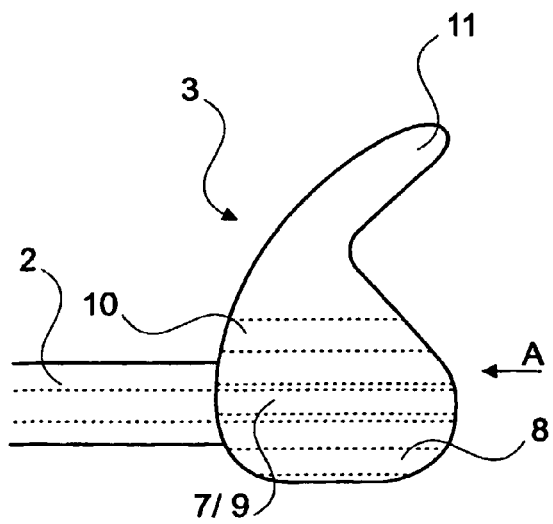
FIG. 18*a* schematically shows the positioning hook of the positioning and insertion instrument without guide bore and with its correction bores and the nose for retention in the medial muscle in frontal view or anterior/posterior view.
Figure 18B:
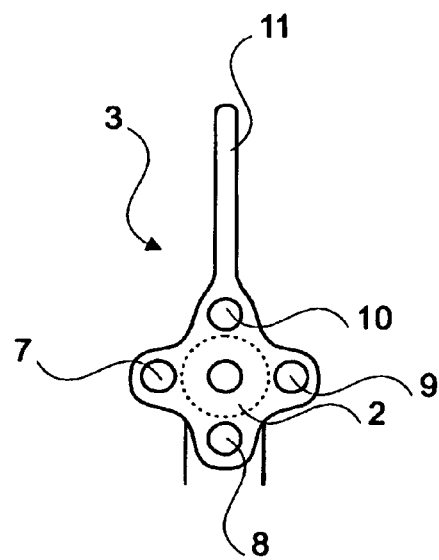
FIG. 18*b* schematically shows the positioning hook of the positioning and insertion instrument without guide bore and with its correction bores and the nose for retention in the medial muscle in view A according to FIG. 18*a*.

FIG. 18a and FIG. 18b show the positioning hook 3 of the positioning and insertion instrument 1, which positioning hook has no guide bore, comprising various correction bores, in particular an anterior/posterior correction bore 7, a medial correction bore 8, a posterior/anterior correction bore 9 and a lateral correction bore 10. In comparison with the variant shown in FIG. 17a and FIG. 17b, the nose tapers somewhat more sharply and is longer. This variant differs in comparison with the variants shown in FIG. 15a and FIG. 15b, FIG. 16a and FIG. 16b, substantially through a smaller cross-sectional area. The correction bores are enclosed by the outer contour.

Figure 19A:
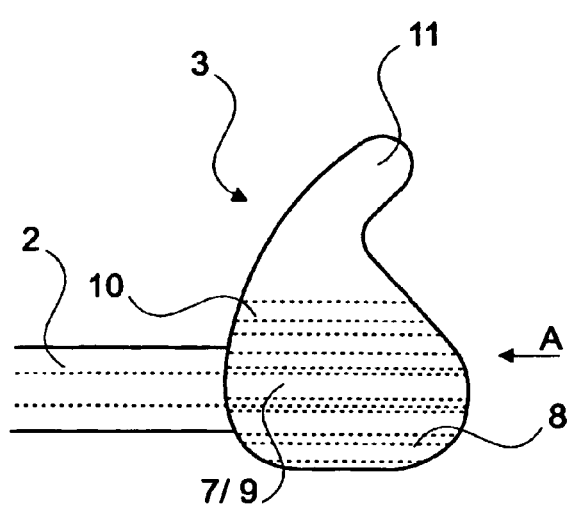
FIG. 19*a* schematically shows the positioning hook of the positioning and insertion instrument without guide bore and with its (additional) correction bores and the nose for retention in the medial muscle in frontal view or anterior/posterior view.
Figure 19B:
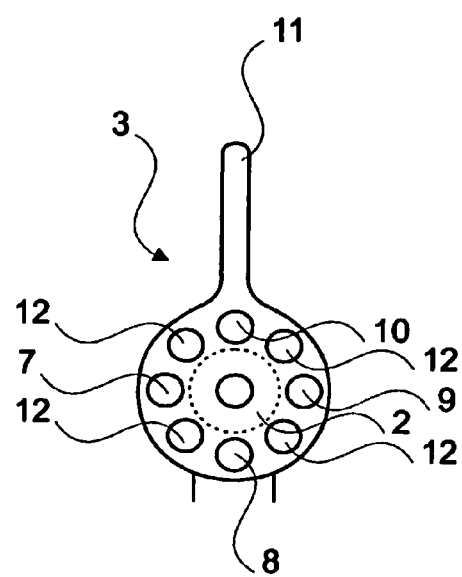
FIG. 19*b* schematically shows the positioning hook of the positioning and insertion instrument without guide bore and with its (additional) correction bores and the nose for retention in the medial muscle in view A according to FIG. 19*a*.

FIG. 19a and FIG. 19b show the positioning hook 3 of the positioning and insertion instrument 1, which positioning hook has no guide bore, comprising various correction bores, in particular an anterior/posterior correction bore 7, a medial correction bore 8, a posterior/anterior correction bore 9, a lateral correction bore 10 and four additional correction bores.

TABLE 1

List of reference numerals

| | |
|---|---|
| 1 | Positioning and insertion instrument |
| 2 | Guide tube |
| 3 | Positioning hook |
| 4 | Retaining arm |
| 5 | Handle |
| 6 | Guide bore |
| 7 | Anterior/posterior correction bore |
| 8 | Medial correction bore |
| 9 | Posterior/anterior correction bore |
| 10 | Lateral correction bore |
| 11 | Nose |
| 12 | Additional correction bore |
| 20 | Opening drill or cutter |
| 30 | T-handle |
| 31 | Drill chuck |
| 32 | Lever |
| 40 | Femur |
| 41 | Trochanter |
| 42 | Angle |
| 43 | Opening |
| 44 | Femur axis |
| 45 | Medial muscle |
| 50 | Guide wire |
| 50a | Reference guide wire |
| 50b | Opening guide wire |
| 50b1 | Further opening guide wire |

While the present invention has been described with reference to the preferred embodiments, those skilled in the art will recognize that numerous variations and modifications may be made without departing from the scope of the present invention. Accordingly, it should be clearly understood that the embodiments of the invention described above are not intended as limitations on the scope of the invention, which is defined only by the following claims.

What is claimed is:

1. A device for positioning and inserting a guide wire into patient tissue comprising:
    a curved guide tube having a distal end configured for insertion into a patient's body to a target position therein, a channel extending through the guide tube between a proximal end configured to receive a first guide wire and a distal guide tube opening in the distal end;
    a handle;
    a retaining arm connecting the guide tube to the handle; and
    a positioning element coupled to the distal end of the guide tube, the positioning element having a guide bore longitudinally aligned with and open to the distal guide tube opening for receiving the first guide wire passed therethrough to a distal positioning element opening which, when the guide tube is in the desired position, opens to a first target location for the insertion of the first guide wire into the bone and a first correction bore extending through the positioning element laterally separated from the guide bore and radially outside the guide tube.

2. The device of claim 1, wherein the positioning element includes at least four correction bores.

3. The device of claim 2, wherein the at least four correction bores are arranged in a concentric circle around the guide tube.

4. The device of claim 1, wherein the positioning element is a positioning hook.

5. The device of claim 1, wherein a distal surface of the positioning element is configured and dimensioned for positioning on a target portion of a surface of a trochanter of a femur for inserting the first guide wire into a femur.

6. The device of claim 5, wherein, when the guide tube is in the desired position, the handle is aligned substantially parallel to a longitudinal axis of a femur.

7. The device of claim 1, wherein an axis of the guide bore is angled between about 6° and about 30° tangentially to a longitudinal axis of the guide tube in the region of its distal end.

8. The device of claim 1, wherein the first correction bores is angled relative to a longitudinal axis of the guide tube in the region of its distal end.

9. The device of claim 1, wherein a distal surface of the positioning element includes a rounded, narrow nose configured to hold the positioning element in muscle tissue while protecting soft tissue.

10. The device of claim 1, wherein the guide tube is curved with a radius of about 300 mm to about 800 mm.

11. A device for positioning and inserting guide wires into a patient's femur comprising:
    a curved guide tube having a distal end configured for placement on one of a trochanter and a medial muscle and a channel extending through the guide tube between a proximal end configured to receive a first guide wire and a distal guide tube opening in the distal end;
    a handle;
    a retaining arm connecting the guide tube to the handle; and
    a positioning hook coupled to the distal end of the guide tube, the positioning hook including a guide bore longitudinally aligned with and open to the distal guide tube opening for receiving the first guide wire passed therethrough to a distal positioning element opening which, when the guide tube is in the desired position, opens to a first target location for the insertion of the first guide wire into the bone and a plurality of correction bores, each of the correction bores extending through the positioning hook laterally separated from the guide bore and radially outside the guide tube.

12. The device of claim 11, wherein the plurality of correction bores are arranged in a concentric circle around the guide tube.

13. The device of claim 11, wherein an axis of the guide bore is angled between about 6° and about 30° tangentially to a longitudinal axis of the guide tube in the region of its distal end.

14. The device of claim 11 wherein the guide tube is curved with a radius of about 300 mm to about 800 mm.

15. The device of claim 11, wherein the positioning hook is releasably connected to the guide tube, and the device further comprises a plurality of positioning hooks configured and dimensioned for placement over another portion of the bone or body tissue.

16. A method for positioning an opening guide wire in an intramedullary canal of a femur comprising:
    loading a first reference guide wire into an insertion device having a curved guide tube with a channel extending therethrough from a proximal end to a distal guide tube opening at a distal end, a handle and a positioning hook coupled to the distal end of the guide tube, the positioning hook having a guide bore longitudinally aligned with and open to the distal guide tube opening and a plurality of correction bores, each of the correction bores extending through the positioning hook laterally separated from the guide bore and radially outside the guide tube;
    placing the positioning hook on a trochanter of the femur;

inserting the first reference guide wire into the trochanter and the center of the intramedullary canal;
removing the insertion device;
loading a second guide wire into the guide tube;
placing the guide bore in the positioning hook over the first reference guide wire;
moving the positioning hook to the trochanter to align the second guide wire at a desired angle relative to the first guide wire.

17. The method of claim 16, wherein, if the second guide wire is not optimally positioned, a correction is carried out by loading a third guide wire into the guide bore; and
placing a selected one of the correction bores over one of the first and second guide wires to align the third guide wire in a new position in the femur.

* * * * *